United States Patent
Morita et al.

(10) Patent No.: US 7,671,868 B2
(45) Date of Patent: Mar. 2, 2010

(54) METHOD AND APPARATUS TO PROVIDE VISUAL CUES INDICATIVE OF THE LEVEL OF SEVERITY OR IMPORTANCE

(75) Inventors: Mark Masao Morita, Arlington Heights, IL (US); William Douglas Hughes, Bainbridge Island, WA (US)

(73) Assignee: General Electric Company, Schenectady, NY (US)

( * ) Notice: Subject to any disclaimer, the term of this patent is extended or adjusted under 35 U.S.C. 154(b) by 380 days.

(21) Appl. No.: 11/679,033

(22) Filed: Feb. 26, 2007

(65) Prior Publication Data

US 2008/0244393 A1 Oct. 2, 2008

(51) Int. Cl.
*G09G 5/00* (2006.01)
*G06F 7/00* (2006.01)
*G06F 17/00* (2006.01)
*G06F 3/00* (2006.01)
*A61N 1/34* (2006.01)
*A61N 1/00* (2006.01)
*A61N 1/08* (2006.01)

(52) U.S. Cl. ............... 345/581; 345/589; 345/619; 345/549; 345/428; 358/518; 358/461; 358/470; 382/165; 382/167; 382/254; 382/274; 707/1; 707/3; 707/100; 707/103; 715/200; 715/700; 715/764; 715/843

(58) Field of Classification Search .......... 345/428, 345/581, 589, 593, 597, 617, 619, 156, 160, 345/549, 556; 358/518, 461, 448, 470; 382/162, 382/165, 167, 182, 218, 254, 260, 274; 707/1, 707/3, 6, 100, 103 Y, 103 Z; 715/200, 273, 715/275, 700, 764, 783, 830, 843; 600/557, 600/27

See application file for complete search history.

(56) References Cited

U.S. PATENT DOCUMENTS

| 5,331,549 | A | 7/1994 | Crawford, Jr. | |
|---|---|---|---|---|
| 2003/0083850 | A1* | 5/2003 | Schmidt et al. | ............ 702/189 |
| 2004/0008219 | A1 | 1/2004 | Sarel | |
| 2006/0044307 | A1* | 3/2006 | Song | ........................ 345/419 |

(Continued)

FOREIGN PATENT DOCUMENTS

DE 10335359 A1 3/2005

(Continued)

*Primary Examiner*—Wesner Sajous
(74) *Attorney, Agent, or Firm*—McAndrews, Held & Malloy, Ltd.; Peter J. Vogel; Michael A. Dellapenna

(57) ABSTRACT

A method of displaying information to relate level of severity or importance comprising the steps of (a) displaying data points; (b) coloring said data points in varying colors according to set levels; and (c) adjusting shades of said colors depending on further defined levels within said set levels. Another method of displaying information to relate level of severity or importance comprising the steps of (a) querying disparate information systems with a certain search parameter (b) displaying data points returned from said search parameter into a single window; (c) coloring said data points in varying colors according to set levels; and (d) adjusting shades of said colors depending on further defined levels within said set levels. A system for displaying information according to level of importance or severity comprising a database, a worklist and an interface wherein said interface conveys level of importance or severity using varying shades of colors.

16 Claims, 4 Drawing Sheets

U.S. PATENT DOCUMENTS

| | | | |
|---|---|---|---|
| 2006/0241720 A1* | 10/2006 | Woods et al. | 607/46 |
| 2008/0120138 A1* | 5/2008 | Morita et al. | 705/3 |
| 2008/0208624 A1* | 8/2008 | Morita et al. | 705/2 |
| 2008/0208630 A1* | 8/2008 | Fors et al. | 705/3 |
| 2008/0208631 A1* | 8/2008 | Morita et al. | 705/3 |
| 2008/0297527 A1* | 12/2008 | Daignault, Jr. | 345/581 |

FOREIGN PATENT DOCUMENTS

| | | |
|---|---|---|
| WO | 2004042596 A1 | 5/2004 |
| WO | 2006050485 A1 | 5/2006 |

* cited by examiner

FIG. 2

| IDX | Da Vinci - Microsoft Internet Explorer | | | | | |
|---|---|---|---|---|---|---|
| File Edit View Favorites Tools Help | | | | | | |
| Back ▾ ⊗ ▾ ⊠ ⊠ ⌂ ⌕ Search ☆ Favorites | | | | | | |
| Address ⌂ http://davinci.idx.com/ | | | | | ▾ | → Go Links» |

| IDX ▾ Dashboard \| Patients \| Inbox \| Alerts | | | | ⌕ ▾ | Search | |
|---|---|---|---|---|---|---|
| Quinn, Mona L · 51 f | □ Exam 19 | | | | | |
| ⌕ Tasks(4)  Care Team | DOB 9-15-1955  MRN 2718-A  HT 168cm  WT 83kg  ALLERGIES 1 2 2 | | | Chart | Orders | Notes |
| ⇦ ⇨ ⊞ ⊞ P ▸ Well Adult Summary ▸ | | | Search | ⚙ Actions ▾ | □ View | |

| Allergies | | Current Medications | | Last 5 Visits | | |
|---|---|---|---|---|---|---|
| Penicillin | Anaphylaxis | Today | Lipitor: 40mg PO QD | 10-21-2005 | Diabetes Check | Out |
| Septra | Rash | Yesterday | Lisonpril: 20mg PO QD | 09-12-2005 | Cold Symptoms | Out |
| Strawberries | Hives | 07-28-2003 | ASA: 81mg PO QD | 04-30-2005 | Painful Feet | Out |
| IVP Dye | Itching | 07-28-2003 | Glucophage: 850mg PO BID | 04-12-2005 | Diabetes Check | Out |
| Erythamycin | GI Distress | | | 01-13-2005 | Non-ketonic Hyperosmo... | In 14d |

Chart

| Last 5 Labs | | Problems | Health Maintenance | | |
|---|---|---|---|---|---|
| 06-02-2005 | Chem12 | 09-18-1989  Diabetes | 04-01-2006 | A1C - Blood Sugar | |
| 06-02-2005 | CBC | 05-05-2003  Hypertension | 01-01-2009 | Colon Cancer Screen | Declined |
| 06-02-2005 | Coags | 09-09-2000  Hyperlipidemia | | | |
| 05-18-2005 | Mammogram | | | | |
| 05-10-2005 | LHand X-ray  ABNL | | | | |

| Vital Signs | | | | | | | Risk Factors | | |
|---|---|---|---|---|---|---|---|---|---|
| | | | | | 100 | | CV Risk Score | Framingham 3% | |
| BP | S D | | | | 63 | | BRAC 2 | Positive | |
| | | 6-2-05 | 5-10-05 | 8-7-04 | 4-8-04 | | | | |
| | | 02:15p | 10:47p | 08:03a | 10:20a | | | | |
| Temp | | 38.2 | 38 | 38.2 | 38 | | | | |
| HR | | 112 | 100 | 132 | 90 | | | 210 | |
| RR | | 18 | 20 | 18 | 22 | | | | |
| BPS/D | | 150/80 | 160/90 | 162/88 | 158/90 | | | | |
| Ht cm | | 182 | 182 | 182 | 182 | | | | |
| Wt kg | | 112 | 110 | 110.5 | 111 | | | | |

| CBC STAT ABNL | Chem 7 STAT | | | | |
|---|---|---|---|---|---|
| 06-26-2002 Final | 06-26-2002 Final | | | | |
| 9.8↓   250↑ | 136 \| 96 \| 12   97 | | | | |
| 16↑       28↑ | 24 \| 3.6 \| 1.1 | | | | |

Done  ⊕Internet

← 200

METHOD AND APPARATUS TO PROVIDE VISUAL CUES INDICATIVE OF THE LEVEL OF SEVERITY OR IMPORTANCE

FIELD OF THE INVENTION

Generally, the technical field involves information systems that display and visualize information and relate level of severity or importance. Specifically, it involves healthcare information systems that provide visual cues toward clinical severity of patient information.

BACKGROUND OF THE INVENTION

Information systems are used in a number of industries to provide a display and/or visualization of a variety of data points. Most of these data points exist as textual data. Quite often, the data points need to be maintained at certain ranges or levels. This requires that the user be able to look at the information system and quickly determine whether the data points require monitoring or intervention. Users must either be familiar with the normal or allowable ranges of each value or reference those ranges. In many situations it is not feasible for an individual to possess the normal ranges for every possible value entered into a certain type of information system. However, it is also not always feasible for the user to reference the allowable ranges due to time constraints.

For example, healthcare information systems currently provide the display and visualization of a variety of patient information, including vital signs, laboratory results, measurements, etc. Physicians, nurses and hospital personnel must either be familiar with the ranges of each value or reference normal ranges when these values appear on a patients chart. Because of the vast amount of information, it is not feasible for an individual to possess the normal ranges for every possible value entered into a healthcare information system. Furthermore, some conditions require immediate attention, creating dangerous time constraints that prevent constant reference to allowable ranges.

Typical communications use the red, yellow and green mapping of a stop light to quickly convey messages to the user. Red coloring can be used to indicate a dangerous or negative level. Yellow coloring can be used to indicate a cautious or neutral level. Green coloring indicates a normal or positive level. Unfortunately, these mappings only communicate absolute values. There is no way to indicate a degree of severity or importance within these broad categories.

In the healthcare context, certain dangerous levels may require immediate physician intervention. For lesser dangerous levels, a physician may not need more than an alert or memo to inform him or her of the condition. Current conventions only communicate the absolute values which may not provide the specificity needed for a physician to make an informed decision.

Accordingly, it would be desirable to develop an information system that quickly indicates the degree of importance or severity of certain data points. In the healthcare field, it would be desirable to develop a healthcare information system that quickly indicates the degree of severity of certain patient information.

SUMMARY OF THE INVENTION

A method of displaying information to relate level of severity or importance made up of the steps of (a) displaying data points; (b) coloring the data points in varying colors according to set levels; and (c) adjusting shades of said colors depending on further defined levels within the set levels.

These steps can be performed sequentially or in some other order. Some possible colors that can be used to indicate levels of importance include green, yellow and red. Ranges for the set levels can be inputted by the user. The number of further defined levels can also be inputted by the user. The ranges for the further defined levels can be inputted by the user. Varying colors could be used in the method. Varying colors can be inputted by the user. The data points can relate to patients' clinical information.

Another method of displaying information to relate level of severity or importance made up of the steps of (a) querying disparate information systems with a certain search parameter; (b) displaying data points returned from the search parameter into a single window; (c) coloring the data points in varying colors according to set levels; and (d) adjusting shades of the colors depending on further defined levels within the set levels.

Those steps can be performed sequentially or in another order. The data points relate to patients' clinical information. The data points can be obtained from disparate hospital departments.

The data points can be organized by subject into column headings. The column headings can display metadata. The metadata can be displayed using a roll over function. The column headings can also filter the data points. The filtered data points can be sorted by color. The user can filter the data points using dynamic keystrokes. The user could alternatively filter the data points using drop down menus.

A system for displaying information according to level of importance or severity made up of a database, a worklist, and an interface wherein said interface conveys level of importance or severity using varying shades of colors.

These and other features of the present invention are discussed or apparent in the following detailed description.

BRIEF DESCRIPTION OF THE DRAWINGS

FIG. 2 illustrates patient information conveyed without color coding of data points.

DETAILED DESCRIPTION OF EMBODIMENT(S)

The current disclosure relates to an information system and method for conveying information that indicates the degree of importance or severity of certain data points. Although a healthcare information system is used as an example, the current disclosure should not be viewed as limited to healthcare related information systems.

Figure 1:
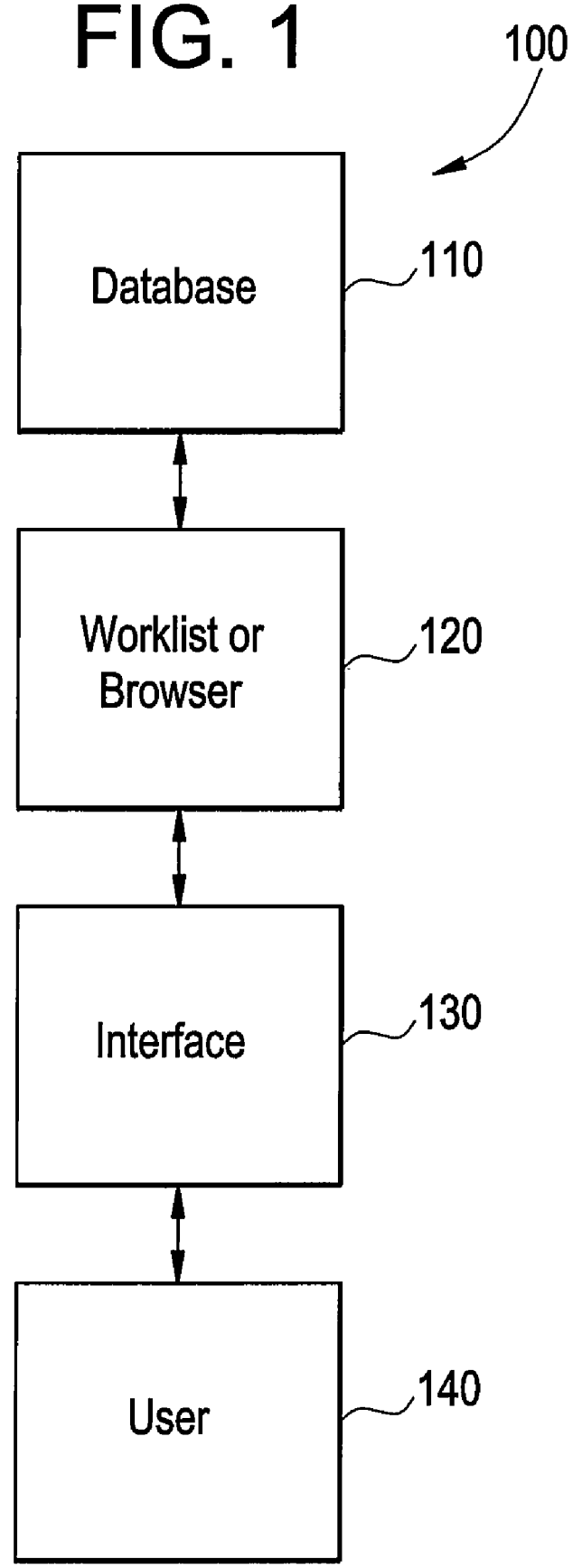
FIG. 1 illustrates a system for displaying information according to level of importance or severity in accordance with an embodiment of the present invention.

FIG. 1 illustrates a system 100 for displaying information according to level of importance or severity in accordance with an embodiment of the present invention. The system includes a database or disparate databases 110, a worklist or browser 120, an interface 130 and a user 140.

The database or databases 110 and the worklist or browser 120 are capable of two way communication with each other.

The worklist or browser 120 is also capable of communicating with the interface 130 and vice versa. The interface 130 is capable of communicating with the user 140. Finally, the user 140 is capable of communicating with the interface 130.

In operation, the database or disparate databases 110 contain information or data points. The data points may pertain to a full department, a portion of a department or a number of departments within the relevant facility. In a healthcare facility, exemplary departments include radiology, cardiology, pharmacy, medication, oncology, pediatrics, physical therapy and lab information. Examples of data points stored in these databases could include patient vital information, medications, test results and medical history.

The worklist or browser 120 queries the database or disparate databases 110 and then aggregates the data from the databases 110. For example, the worklist or browser 120 could query all of the disparate hospital systems regarding a certain patient. The databases would return the information for that patient. The worklist or browser 120 would then aggregate the data points for that patient. All of the information for that patient would be compiled and readily available.

In one embodiment, the database 110 may be accessed when information is needed by a worklist or browser 120 in a "pull" model. In another embodiment, the database 110 may provide information to a worklist or browser 120, in a "push" model when some changes are made to information in the database 110.

Next the worklist or browser 120 aggregates the data into a single, interactive window or interface 130. The interface 130 may communicate some or all of the data points to the user 140. The interface 130 may include a display device. The data points are displayed for quick interpretation and understanding by the user 140.

Possible display devices include computer screens, portable computers, tablet computers, and/or personal digital assistants (PDA's). The interface 130 may include an input device. For example, the input device may include one or more of a keyboard, a touchscreen, a joystick, a mouse, a touchpad, and a microphone.

An information system 100, such as a healthcare information system, can achieve a full display of data points relating to a certain topic, for example a certain patient, from a variety of disparate information systems. A worklist or browser 120 queries disparate information systems and aggregates the data into a single, interactive window that displays the results and data points from a particular search. In the health industry, the worklist or browser 120 would query the enterprise hospital systems for information on a certain patient. Some examples of enterprise hospital systems include radiology, cardiology, pharmacy, medication, and lab information. The worklist or browser then aggregates the data into a single, interactive window displaying the results and data points for a particular patient search.

As discussed above, it is desirable to display these data points in such a way that the display quickly indicates the degree of importance or severity of certain data points. Data points have previously been illustrated with the red, yellow and green mapping of a stop light to convey messages to the user. Unfortunately, these mappings only communicate absolute values. In many situations a user wants more granularity than this system provides.

FIG. 2 illustrates a patient information system that conveys data points without color coding 210. This display makes it extremely difficult for the user, for example a physician or other hospital employee, to interpret at a quick glance which data points require monitoring or intervention. FIG. 2 illustrates the desire to provide visual cues for importance or severity of data points in an information system. This is particularly true in industries where the information is monitored and assessed quickly such as the healthcare industry.

Certain embodiments utilize varying shades of indicative colors such as red, yellow and green to color different data points depending on the severity or importance of the data point. The lightness or darkness of the shade indicates the importance of the data point. For example, normal levels of severity or importance can be indicated by green, slightly low levels indicated by light green, slightly high levels by dark green, cautionary levels indicated by yellow, less cautionary levels indicated by light yellow, dangerous levels indicated by red, less dangerous levels indicated by light red and extremely dangerous levels indicated by dark red. This system allows more granularity and precision than the standard red, yellow, or green system.

Figure 3:
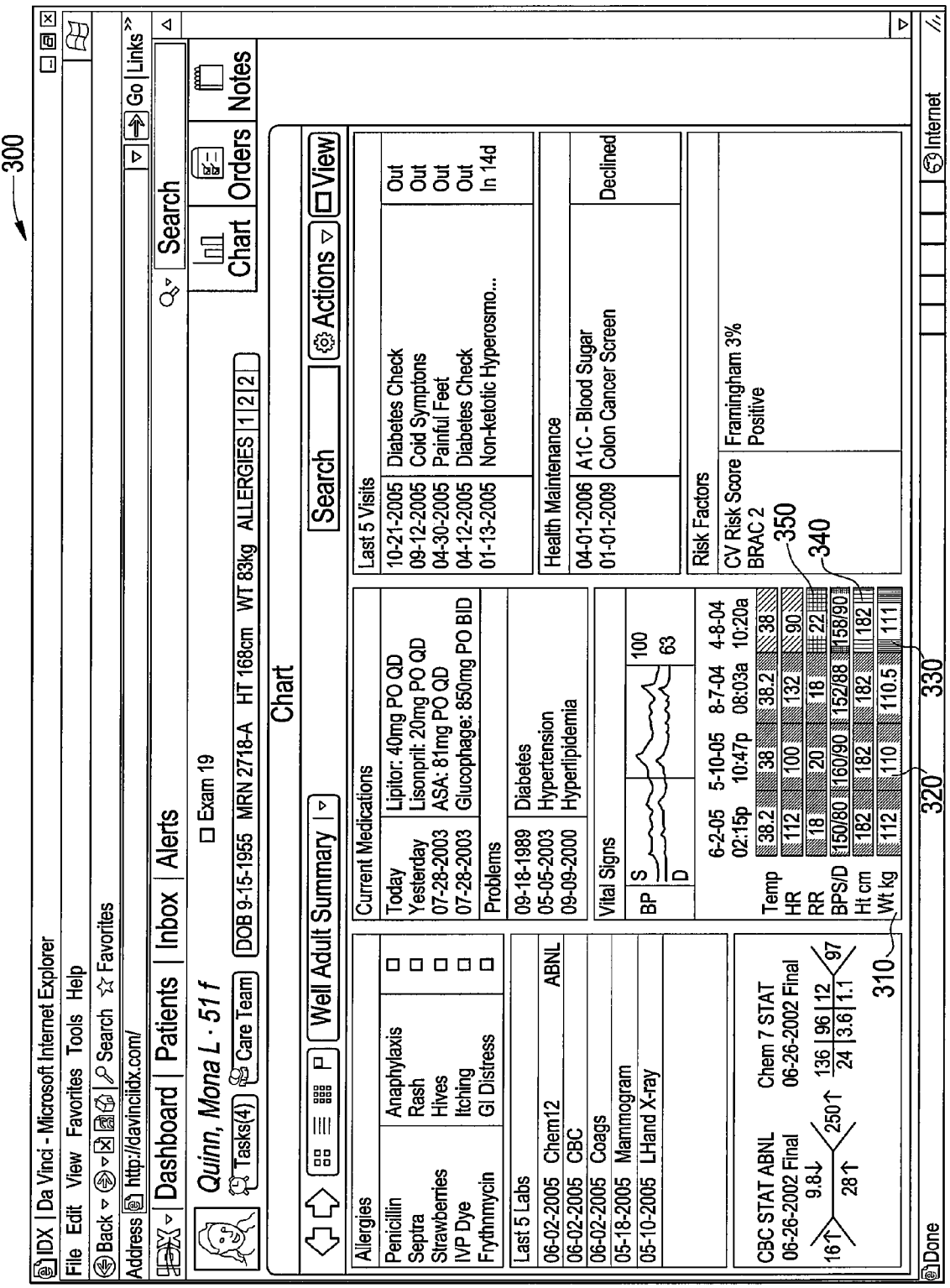
FIG. 3 illustrates color coding attached to metrics that correspond to a patient's vital signs in accordance with an embodiment of the present invention.

FIG. 3 illustrates a patient information system 300 that uses color coding of attached data points that correspond to a patient's information 310. At a quick glance the user, for example a physician or other care provider, could determine which items are normal (indicated by green) 320, cautionary (indicated by yellow), dangerous (indicated by red) 330, less cautionary (indicated by light yellow) 350 and less dangerous (indicated by light red) 340. FIG. 3 uses narrowly spaced diagonal lines to represent green, widely spaced diagonal lines to represent light green, narrowly spaced vertical lines to represent red, broadly spaced vertical lines to represent light red, a small lattice to represent yellow and a large lattice to represent light yellow.

The system can be configured to allow the user to input ranges for the various levels in accordance with an embodiment of the present invention. This would allow the user to decide which ranges of data points fall into which category. For example the user would be able to input values for the cautious, less cautious, dangerous, less dangerous, normal, and slightly abnormal levels. The data points would then be displayed in the corresponding colors according to the user's specific ranges.

The system can also be configured to allow the user to increase or decrease the granularity of the display. The user could input a level of granularity and the display would use a wider or narrower variety of shades of each color to indicate the level of importance or severity with more or less specificity. If the user desires a lower level of granularity, he or she would indicate this preference and there would be less shades of each color. If the user desires a higher level of granularity, he or she would indicate this preference and there would be more shades of each color.

Colors other than red, green and yellow could alternatively be used. The system could be configured to allow the user to add additional colors to indicate levels other than those mentioned above. The user could input the other colors to be used and which data point to use with the other colors. The data points would then be displayed using the alternative colors with the varying shades to indicate varying levels. The user could also input ranges for the other colors and granularity levels as discussed above.

Data points could be organized on the display under column headings. For example, data points dealing with cardiology could be under one column heading while those dealing with medication could be under another. These column headings could be user configurable to display metadata relevant to a specific user. This could give the user a quick glance overview of a certain data points under a certain column. One way this could be done is by using a roll over function. A roll over function would present more data about a certain column heading when the user passes his or her cursor over the column heading.

The column heading could also filter the data points via dynamic keystrokes or specific drop down menus related to each column heading. This would allow the user to sort the data points under a specific column heading by color or search the data points by color. A drop down menu could give the user the option of arranging from most important to least important and vice versa. By using the cursor the user could select the desired layout and the data points would be sorted accordingly. Dynamic keystrokes, pushing certain combinations of keys, could also be used to allow the user to sort the data points under a certain column heading.

In another embodiment of the present invention, the interface 130 may communicate the dangerous levels or highly important data points to the user 140 using specialized messages. The interface 130 may display a pop-up window or overlay, email or page the user 140, and/or generate a printed, displayed and/or transmitted report, for example.

In certain embodiments, one kind of user may have different access and modification capabilities than another user. For example, a staff member may only be permitted to access some kinds of resource information from the interface 130, while a supervisor may have access to all of the resource information and be able to allocate resources. Furthermore, a supervisor may have the ability to change settings or ranges while a staff member may only view information.

Figure 4:
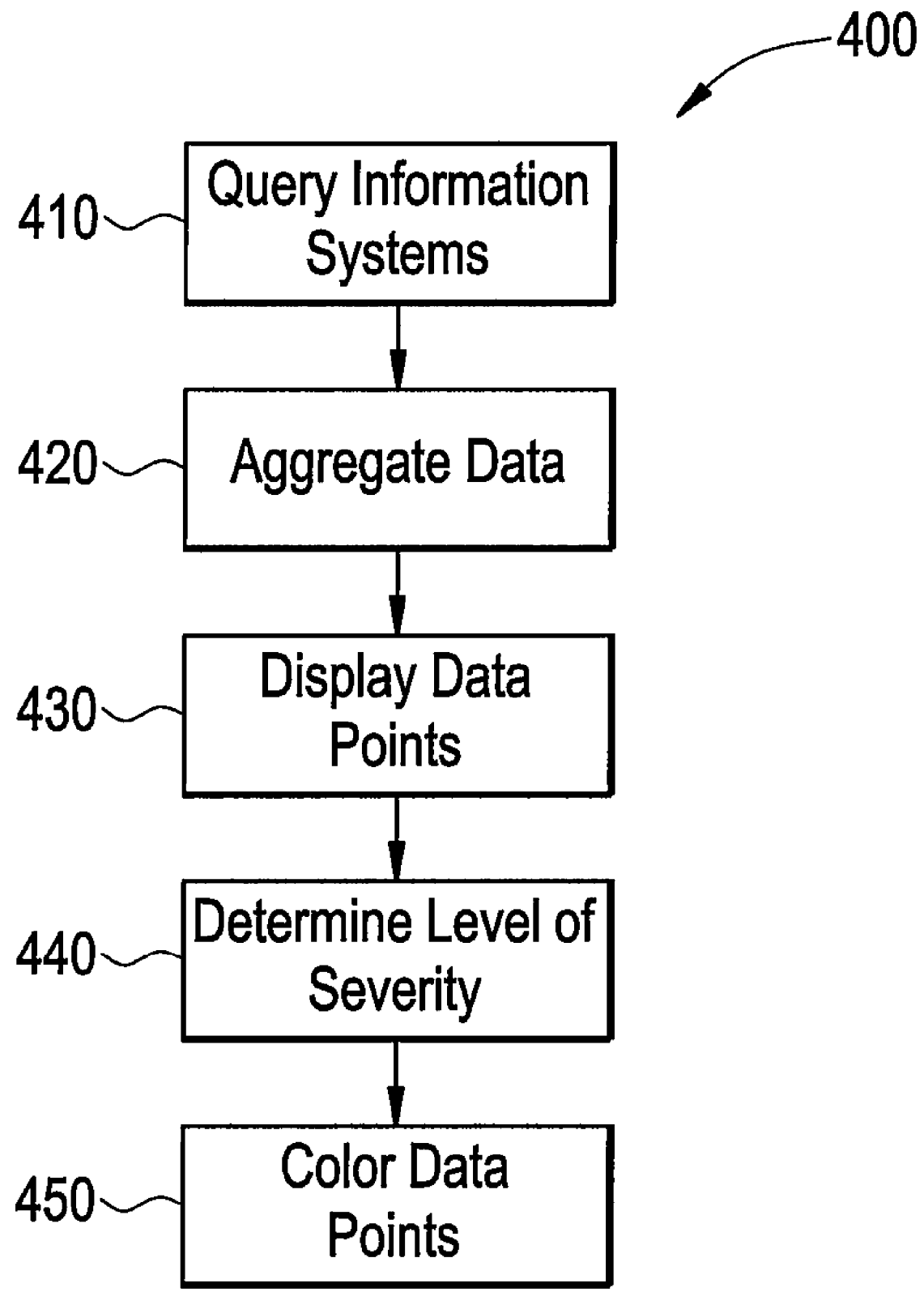
FIG. 4 illustrates a flow diagram for a method of displaying information according to level of importance or severity in accordance with an embodiment of the present invention.

FIG. 4 illustrates a flow diagram for a method of displaying information according to level of importance or severity in accordance with an embodiment of the present invention. The method includes the following steps that will be described in more detail below. First, at step 410, information systems are queried. Second, at step 420, data is aggregated from the queried systems. Third, at step 430, the data points are displayed. Fourth, at step 440, the level of severity or importance is determined for each data point. Finally, at step 450, the data points are colored in varying shades according to the level of severity or importance.

In the first step 410, the information system is queried. The information system may be a database, disparate databases or some other means of data storage. The information system contains or stores information or data points. The data points may pertain to a full department, a portion of a department or a number of departments within the relevant facility. In a healthcare facility, exemplary departments include radiology, cardiology, pharmacy, medication, oncology, pediatrics, physical therapy and lab information. Examples of data points stored in these databases could include patient vital information, medications, test results and medical history.

Querying the information system make it possible to move on to the next step 420, aggregating the data points. As explained above, aggregating the data points from disparate databases would allow healthcare professionals to compile the data points for a certain patient making all of that patient's information readily available. The information systems could be queried and then aggregated using either a "push" or "pull" model, depending on the user's needs.

In the next step 430, the aggregated data points are displayed. The display may show some or all of the data points. The data points are displayed for quick interpretation and understanding. Possible display devices include computer screens, portable computers, tablet computers, and/or personal digital assistants (PDA's).

In the next step 440, the data points are classified according to level of importance of severity. The data points are sorted into ranges. These ranges may be determined by the individual user or may be pre-set. The ranges indicate the level of severity or importance for the data points. For example, the data points could be sorted according to whether the level is slightly dangerous, dangerous, highly dangerous, cautious, slightly cautious or normal.

In the final step 450 the data points are colored in varying shades of a color depending on the level of severity or importance. The color coding utilizes varying shades of indicative colors such as red, yellow and green to color different data points depending on the severity or importance of the data point. The lightness or darkness of the shade indicates the importance of the data point. For example, normal levels of severity or importance can be indicated by green, slightly low levels indicated by light green, slightly high levels by dark green, cautionary levels indicated by yellow, less cautionary levels indicated by light yellow, dangerous levels indicated by red, less dangerous levels indicated by light red and extremely dangerous levels indicated by dark red.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. A method of displaying information to relate levels of clinical severity comprising the steps of:
   displaying data points with a display;
   defining a plurality of different colors, the colors corresponding to different levels of clinical severity;
   defining a plurality of granularities for the corresponding different colors, the granularities corresponding to degrees of the different levels of clinical severity;
   coloring the data points with the plurality of different colors to indicate each of the different levels of clinical severity;
   adjusting a shade of a colored data point according to the corresponding amount of granularity to indicate the degree of level of clinical severity; and
   providing for a user to input the amount of granularities.

2. The method of claim 1 wherein said steps are performed sequentially.

3. The method of claim 1 wherein the colors comprise green, yellow and red, and the colors indicate increasing levels of importance.

4. The method of claim 1 wherein corresponding ranges for the levels of clinical severity are inputted by the user.

5. The method of claim 1 wherein ranges for the granularities are inputted by the user.

6. The method of claim 1 wherein said varying colors are inputted by the user.

7. The method of claim 1 wherein said data points relate to clinical information of a patient.

8. A method of displaying information to relate levels of clinical severity comprising the steps of:
   querying disparate information systems with a search parameter;
   displaying data points returned from said search parameter into a window on a display;
   coloring said data points with different colors to indicate each of the different levels of clinical severity;
   adjusting shades of said colors depending on further defined levels within said set levels;
     organizing said data points in at least one column having a column heading; and
     displaying metadata over said at least one column using a roll-over function.

9. The method of claim 8 wherein said steps are performed sequentially.

10. The method of claim 8 wherein said column headings filter said data points.

11. The method of claim 10 wherein said data points are sorted by color.

12. The method of claim 10 wherein a user filters said data points using dynamic keystrokes.

13. The method of claim 10 wherein the user filters said data points using drop down menus.

14. The method of claim 8 wherein said data points relate to patients' clinical information.

15. The method of claim 14 wherein said data points are obtained from disparate hospital departments.

16. A system for displaying information according to level of importance or severity comprising:
    a database comprising data points;
    a worklist in communication with said database, and capable of aggregating said data points;
    an interface for displaying the aggregated data points in a plurality of different colors and shades, the colors corresponding to levels of clinical severity, and the shades corresponding to a granularity indicating a degree of levels of clinical severity
    wherein said interface conveys level of importance or severity using varying shades of colors.

* * * * *